United States Patent [19]

Kotitschke et al.

[11] 4,272,523
[45] * Jun. 9, 1981

[54] FRACTIONATING CITRATE-STABILIZED PLASMA

[75] Inventors: Ronald Kotitschke; Wolfgang Stephan, both of Dreieich, Fed. Rep. of Germany

[73] Assignee: Biotest Serum Institut GmbH, Frankfurt-Niederrad, Fed. Rep. of Germany

[*] Notice: The portion of the term of this patent subsequent to Mar. 28, 1995, has been disclaimed.

[21] Appl. No.: 75,867

[22] Filed: Sep. 17, 1979

Related U.S. Application Data

[63] Continuation-in-part of Ser. No. 875,489, Feb. 6, 1978, Pat. No. 4,170,590, which is a continuation-in-part of Ser. No. 639,960, Dec. 11, 1975, Pat. No. 4,081,431.

[30] Foreign Application Priority Data

Jan. 20, 1979 [DE] Fed. Rep. of Germany ....... 2902158

[51] Int. Cl.³ .................... A61K 35/14; C07G 7/00
[52] U.S. Cl. ................................ 424/101; 260/112 B
[58] Field of Search ................... 260/112 R, 112 B; 424/101

[56] References Cited

U.S. PATENT DOCUMENTS

| | | | |
|---|---|---|---|
| 3,652,530 | 3/1972 | Johnson et al. | 260/112 B |
| 3,682,881 | 8/1972 | Fekete et al. | 260/112 B |
| 3,869,436 | 3/1975 | Falksneden | 260/112 B |
| 3,916,026 | 10/1975 | Stephan | 424/177 |
| 3,920,625 | 11/1975 | Anderson et al. | 260/112 B |
| 3,973,002 | 8/1976 | Hagan et al. | 260/112 B X |

OTHER PUBLICATIONS

Laursen et al., Chem. Abstr. 67,50,325 (1967).
Reid et al., Ind. & Eng. Chem. 43, No. 5 (1951) 1074 & 1075.
Tullis et al., The New England Journal of Medicine 273, No. 13 (1965) 667–674.

Primary Examiner—Delbert R. Phillips
Attorney, Agent, or Firm—Sprung, Felfe, Horn, Lynch & Kramer

[57] ABSTRACT

The present invention relates to a method for making fibrinogen, a prothrombin complex containing the coagulation factors II, VII, IX and X that can contain antithrombin III, antithrombin III and a solution of stable serum proteins from a blood plasma stabilized with citrate which is characterized in that from the plasma, by adsorption on colloidal silica of a specific surface of 50 to 400 m²/g and a concentration of 50 to 400 mg per g plasma protein, fibrinogen is isolated; and in that thereupon (a) citrate and calcium ions are removed by ultrafiltration or dialysis and then from the protein solution, over anion exchangers or tricalcium phosphate that adsorb proteins, the coagulation factors II, VII, IX and X and antithrombin III are adsorbed, or (b) the coagulation factors II, VII, IX and X are adsorbed prior to the ultrafiltration or dialysis, antithrombin III then not being simultaneously adsorbed, and antithrombin III is adsorbed on the said adsorbents after the removal of the citrate and calcium ions by ultrafiltration or dialysis; and in that thereupon from the remaining plasma fluid further unstable proteins are removed by another adsorption on colloidal silica and a solution of stable serum proteins is obtained.

16 Claims, 6 Drawing Figures

FRACTIONATING CITRATE-STABILIZED PLASMA

This is a continuation-in-part of Application Ser. No. 875,489, filed Feb. 6, 1978, now U.S. Pat. No. 4,170,590, which is a continuation-in-part of Ser. No. 639,960, filed Dec. 11, 1975, now U.S. Pat. No. 4,081,431.

The present invention relates to a method for making fibrinogen, a prothrombin complex containing the coagulation factors II, VII, IX and X that can contain antithrombin III, antithrombin III and a solution of stable serum proteins from a blood plasma stabilized with citrate which is characterized in that from the plasma, by adsorption on colloidal silica of a specific surface of 50 to 400 m$^2$/g and a concentration of 50 to 400 mg per g plasma protein, fibrinogen is isolated; and in that thereupon (a) citrate and calcium ions are removed by ultrafiltration on dialysis and then from the protein solution, over anion exchangers or tricalcium phosphate that adsorb proteins, the coagulation factors II, VII, IX and X and antithrombin III are adsorbed, or (b) the coagulation factors II, VII, IX and X are adsorbed prior to the ultrafiltration or dialysis, antithrombin III then not being simultaneously adsorbed, and antithrombin III is adsorbed on the said adsorbents after the removal of the citrate and calcium ions by ultrafiltration or dialysis; and in that thereupon from the remaining plasma fluid further unstable proteins are removed by another adsorption on colloidal silica and a solution of stable serum proteins is obtained. In the method according to the invention there are obtained from a blood plasma stabilized with citrate, while avoiding the clotting process, three coagulation-active, hepatitis-safe and therapeutically usable protein preparations and one coagulation-inactive, hepatitis-safe serum or solution of stable serum proteins. The three coagulation-active preparations are:

1. Fibrinogen
2. Prothrombin complex (coagulation factors II, VII, IX, and X, possibly containing AT III)
3. Antithrombin III (AT III).

The coagulation factors II, VII, IX and X are also called PPSB factors in which

P=prothrombin (factor II)
P=proconvertin (factor VII)
S=Stuart-Prower factor (factor X)
B=antihemophilic globulin B (factor IX).

In U.S. Pat. No. 4,081,431 a method is described for making a concentrate containing antihemophilic globulin A in addition to a prothrombin complex and a solution of stable serum proteins in which as starting material a frozen ion exchange plasma is used which is thawed again at temperatures between 2° and 8° C. and from which the supernatant plasma fluid is separated from the factor-VIII-containing protein and this cryoprecipitate processed in the known per se manner to a factor-VIII concentrate, while the plasma fluid is freed from the factors II, VII, IX and X by adsorption over commercial tricalcium phosphate, and then from the plasma fluid, over colloidal silica with a specific surface of 50 to 400 m$^2$/g, the still remaining coagulation factors and other unstable proteins are adsorbed and a solution of stable serum proteins remains behind.

In Application Ser. No. 875,489, a variation of the above-described method is proposed in which as starting material a conventional citrate plasma is used and after thawing and separating of the cryoprecipitate the supernatant is treated with polystyrene/divinylbenzene/quaternary amine-based anion exchange resins and polystyrene/sulfonate-based cation exchange resins. In this method, citrate plasma is thus converted to ion exchange plasma which, besides antihemophilic globulin A, prothrombin complex and stable serum proteins, will yield fibrinogen.

Surprisingly, it was now found that not only ion exchange plasma—as used in the aforesaid applications—but also a citrate plasma adsorbed over colloidal silica with a specific surface of 50 to 400 m$^2$/g and dialyzed or ultrafiltered can be used for making fibrinogen, a prothrombin complex containing the coagulation factors II, VII, IX and X and a solution of stable serum proteins.

The prothrombin complex as obtainable by the method according to the invention contains additionally antithrombin III, which can be separated from the factors II, VII, IX and X and obtained as additional product. After a stepwise elimination of the coagulation factors from the citrate plasma the solution of stable serum proteins is obtained.

It is also possible to make antithrombin III side by side with prothrombin complex, without first having to make an antithrombin III-containing prothrombin complex.

German Pat. Nos. 16 17 319 and 16 17 335 describe the use of colloidal silica in a concentration of 250 to 500 mg per gram total protein at temperatures of 20° to 50° C. for the removal of lipoproteins and fibrinogen. The object of those said patents is the production of stable and sterile serum protein solutions.

Surprisingly, it was now found that when using low concentrations of colloidal silica in the adsorption of citrate plasma at temperatures between about 1° and 37° C. fibrinogen is attached practically specifically to the colloidal silica, while the coagulation factors II, VII, IX and X remain preserved in the "residual citrate plasma" freed from the colloidal silica. This separation takes place particularly well at temperatures between about 2° and 6° C., and particularly about 4° C.

The removal of the fibrinogen from the citrate plasma makes it possible to dialyze or ultrafilter this "citrate plasma" so as to remove the citrate and calcium ions from this "plasma". A dialysis or ultrafiltration of a fibrinogen-containing citrate plasma is not possible because the removal of the citrate stabilizer, even in the absence of calcium ions, leads to fibrinogen precipitations which clog the membranes and thus make dialysis or ultrafiltration practically impossible.

The invention will be further described with reference to the accompanying drawings, wherein.

Figure 1:
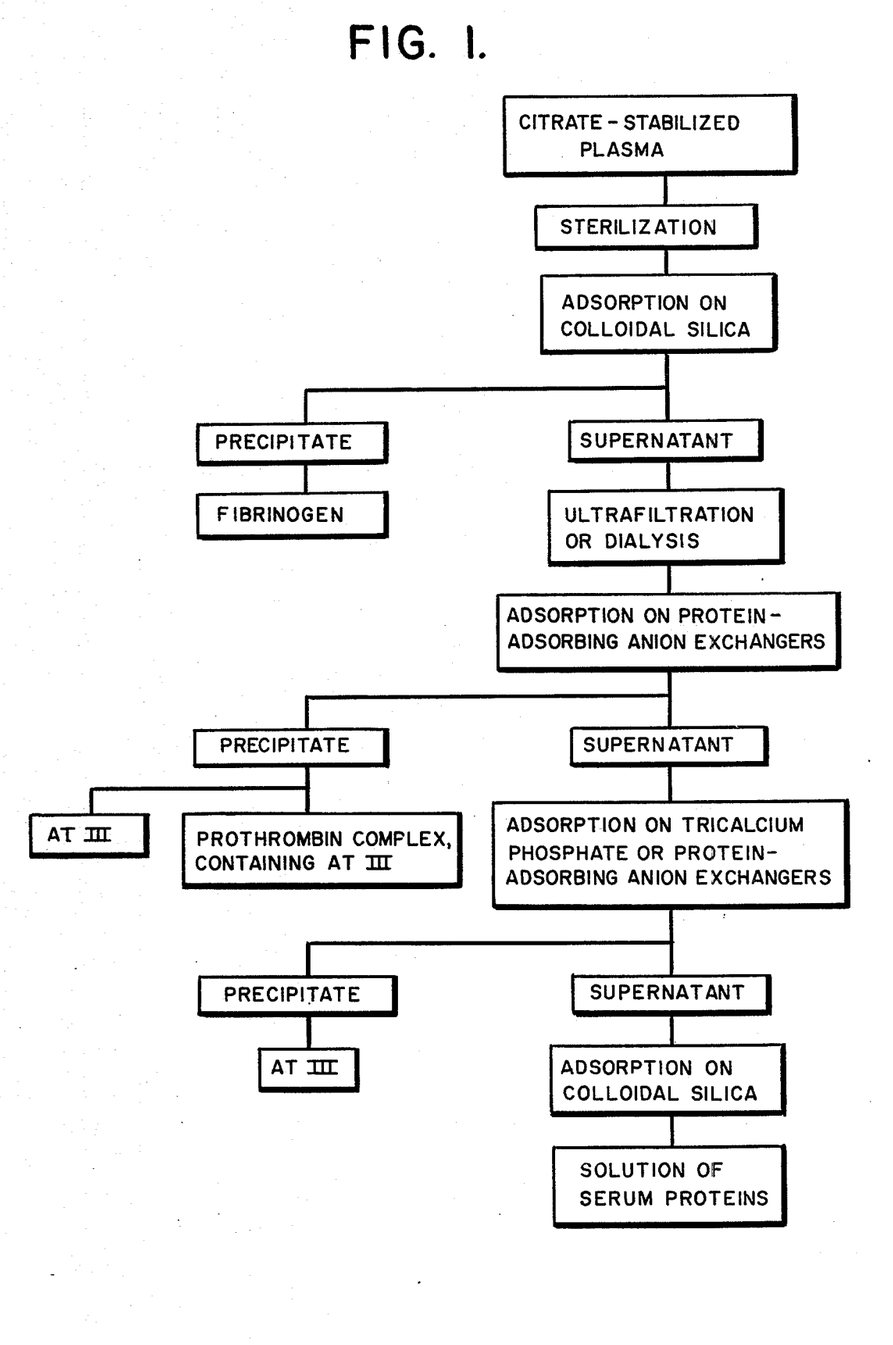
FIG. 1 is a flow sheet of one process for fractionating a citrate-stabilized plasma.

Referring now more particularly to FIG. 1, the following Table I shows the concentration of fibrinogen and the factors II, VII, IX and X as well as factor XII as a function of the concentration of the colloidal silica ("Aerosil AE 380", registered trademark of Degussa) used in the adsorption under the conditions of the method according to FIG. 1 and the conditions given in German Pat. Nos. 16 17 335 and 16 17 319. As starting material a, an untreated citrate plasma pool was used, and as starting material b a citrate plasma pool treated with beta-propiolactone and ultraviolet radiation was used. Treatment of plasma with beta-propiolactone and ultraviolet radiation reduces indeed the activity of the coagulation factors (R. Kotitschke and W. Stephan: Structure and Function of Fibrinogen. Schattauer-Verlag, Stuttgart-New York 1976, P. 222-228); this treatment with beta-propiolactone and ultraviolet radiation serves, however, for the sterilization and inactivation of any still remaining viruses in the plasma and, in particular, for assuring freedom from hepatitis of the protein factors.

TABLE I

Concentration of coagulation factors as a function of the concentration of colloidal silica used in the adsorption

| Silica | Activity of the factors in % of the norm | | | | | Fibrinogen |
|---|---|---|---|---|---|---|
| mg/g protein | II | VII | IX | X | XII | mg/100 ml |
| 0 (Starting material a+) | 100 | 100 | 100 | 100 | 100 | 320 |
| 250 at +4° C. | 95 | 92 | 98 | 95 | 0 | 0 |
| 500 at 45° C. | 0 | 0 | 0 | 0 | 0 | 0 |
| 0(Starting material b++) | 50 | 60 | 60 | 55 | 55 | 200 |
| 250 at +4° C. | 45 | 55 | 55 | 50 | 0 | 0 |
| 500 at +45° C. | 0 | 0 | 0 | 0 | 0 | 0 |

+Human citrate plasma pool
++Human citrate plasma pool treated with beta-propiolactone and ultraviolet radiation The term "residual citrate plasma" poses certain problems of nomenclature since "plasma" usually means a protein solution which still contains fibrinogen in coagulable form. A fibrinogen-free protein solution is usually identified as a serum so "residual citrate plasma" could just as well be called "residual citrate serum". "Serum", however, usually identifies the protein solution that results from a plasma or blood after the clotting process is completed, but in the protein solution treated with colloidal silica adsorbent according to the invention the coagulation factors II, VII, IX and X still exist as proenzymes and/or in activatable form and thus can also be used further for a clotting process, while the fibrinogen no longer is present.

If now by dialysis or ultrafiltration the citrate originally required for the stabilization of the blood and also the calcium ions are removed from the colloidal silica-adsorbed protein solution, a stabilizer-free protein solution is obtained which still contains coagulation-active coagulation factors.

The following Table II shows the composition of the citrate plasma and of the solutions obtained after adsorption on colloidal silica and ultrafiltration with regard to the content in protein, fibrinogen, citrate and calcium ions.

TABLE II

| Content in: | Protein g/100 ml | Fibrinogen mg/100 ml | Citrate meq/l | $Ca^{++}$ meq/l |
|---|---|---|---|---|
| Citrate plasma | 5.65 | 320 | 60 | 4.5 |
| After SiO2 ads. | 5.29 | 0 | 60 | 4.4 |
| After ultrafilt. | 5.20 | 0 | 0.5 | 0.30 |

The different behavior of a normal citrate plasma as compared to a colloidal silica-adsorbed and ultrafiltered citrate plasma is also made clear from the following Table III. With 1.5 g DEAE-Sephadex A-50 per 1 l plasma, about 8% of the proteins are adsorbed out of the citrate plasma, while from silica-adsorbed and ultrafiltered plasma under the same conditions about 23% of the plasma proteins are adsorbed.

TABLE III

| | Protein concentration in g/100 ml | |
|---|---|---|
| | Citrate plasma normal | Citrate plasma adsorbed on $SiO_2$ and ultrafiltered |
| Start | 5.65 | 5.20 |
| DEAE-Sephadex A-50 (1.5 g/l) | 5.20 | 4.00 |
| DEAE-Sephadex A-50 (0.5 g/l) | 5.40 | 4.70 |

From the solution obtained after $SiO_2$ adsorption and ultrafiltration or dialysis the coagulation factors II, VII, IX and X as well as antithrombin III can be adsorbed on tricalcium phosphate or, surprisingly, also on protein adsorbing anion exchangers, particularly cross-linked dextrans or cellulose carrying diethylaminoethyl groups, e.g. "DEAE-Sephadex" or "DEAE-cellulose."

The following Table IV shows a comparison between the adsorbability of antithrombin III from normal citrate plasma and that from colloidal silica-adsorbed and ultrafiltered citrate plasma. As colloidal silica, "Aerosil 380" (AE 380) was used.

TABLE IV

| | Adsorbability of AT III | |
|---|---|---|
| | AT III in citrate plasma normal ($IU^+$/ml) | AT III in citrate plasma AE 380, ultrafiltered ($IU^+$/ml) |
| Starting material | 19.1 | 19.1 |
| After adsorption with "DEAE-Sephadex A 50" | 17.5 | 10.3 |

+IU = inhibitor units as determined with a peptide substrate (Tos—Gly—Pro—Arg—pNA)

The antithrombin III together with the PPSB factors can be eluted from the tricalcium phosphate or the protein-adsorbing anion exchangers by means of citrate-containing solutions. The importance of this discovery lies in the fact that previous PPSB preparations without antithrombin III carried an inherent risk of thrombosis (S. Chandra and M. Wickerhauser: Preparation of a Nonthrombogenic Prothrombin Complex Concentrate. Thrombos. Heamostas. VI Int. Cong. Schattauer Verlag, Stuttgart-New York, 1977, P. 219).

It was for this reason that in recent years the demand was made to check PPSB preparations by appropriate tests for thrombosis risks. To that end, the $TGt_{50}$ time as measure for thrombosis risk was introduced. With this $TGt_{50}$ time the incubation time is determined as required for reaching a fibrinogen coagulation time of 50 seconds. Thus with this means, the formation of thrombin is determined. (J. D. Cash, G. Sas, R. G. Dalton a. R. Owens: Thrombogenicity of Factor IX Concentrates. Workshop on inhibitors of factors VIII and IX, Vienna 26.-27.1.1976, P.112-117).

PPSB preparations without antithrombin III have $TGt_{50}$ times below 20 minutes when made from citrate plasma using "DEAE-Sephadex", whereas the corresponding antithrombin III-containing PPSB preparations from Aerosil-adsorbed and ultrafiltered citrate plasma have $TGt_{50}$ times of over 5 hours.

In the known methods as described in the literature (J. Heystek, H. G. J. Brummelhuis, H. W. Krijnen:

Contributions to the Optical Use of Human Blood. II. The Large-Scale Preparation of Prothrombin Complex. A Comparison between 2 Methods Using the Anion Exchangers DEAE-Cellulose DE 52 and DEAE-Sephadex A 50. Vox.Sang.25: No. 2 P.113–123 (1973)) for making PPSB from citrate plasma using "DEAE-Sephadex A 50" or "DEAE-Cellulose", the PPSB factors were eluted from the adsorbent with citrate/NaCl buffer solutions. Surprisingly, it was now found that—as shown in Table IV—antithrombin III is also adsorbed on protein-adsorbing anion exchange resins, e.g. "DEAE-Sephadex A 50" or "DEAE-Cellulose", if the citrate ion concentration in the citrate plasma is substantially lowered. Table V shows how decisive the citrate concentration is for the antithrombin III-adsorbability on the said adsorbents.

TABLE V

AT III adsorbability on "DEAE-Sephadex A 50" as a function of citrate concentration in an "Aerosil 380" adsorbed and then dialyzed or ultrafiltered citrate plasma.

| Citrate | AT III in IU/ml | |
|---|---|---|
| | Before DEAE-Sephadex adsorption | After DEAE-Sephadex adsorption |
| 63 | 17.5 | 17.0 |
| 10 | 17.5 | 16.8 |
| 2.5 | 17.5 | 15.9 |
| 0.5 | 17.5 | 10.5 |

The data of Table V explain also the surprising discovery that according to FIG. 1, for example, an antithrombin III preparation can be obtained in that colloidal silica-adsorbed and then ultrafiltered or dialyzed citrate plasma is adsorbed with protein-adsorbing anion exchangers, e.g. "DEAE-Sephadex A 50", and the adsorbed antithrombin III is then eluted by low citrate concentrations, e.g. 0.01 M citrate in physiological NaCl solution. Under these conditions, the PPSB factors are not eluted from "DEAE-Sephadex". As a function of the citrate concentration of the eluent, antithrombin III is eluted to a greater or lesser extent. Since for the abovestated reasons it is desirable to have antithrombin III in the PPSB (reduction of thrombosis risk) a citrate concentration in the elution of antithrombin III from protein-adsorbing anion exchangers for making an antithrombin-III concentrate will be chosen in which the antithrombin III is not entirely eluted but some of it remains on the protein-adsorbing anion exchangers and is only completely eluted from the said anion exchangers along with the PPSB factors.

The fibrinogen adsorbed on the colloidal silica can be eluted with buffer solutions containing about 5 to 20% of alkali metal or ammonium halides, e.g. about 10 to 20% common salt solutions containing citrate, at pH values of about 8.0 to 10.0. Coagulable fibrinogen can be obtained by ultrafiltration of these solutions and subsequent alcohol fractionation.

By renewed adsorption with colloidal silica according to the conditions stated in the aforementioned patents or different adsorption conditions relative to SiO$_2$ concentration, temperature and time, from the protein solution previously adsorbed by tricalcium phosphate or protein-adsorbing anion exchangers, by adsorption of lipids there is obtained a solution of stable serum proteins which is free from coagulation factors or metabolites of the coagulation factors.

Figure 2:
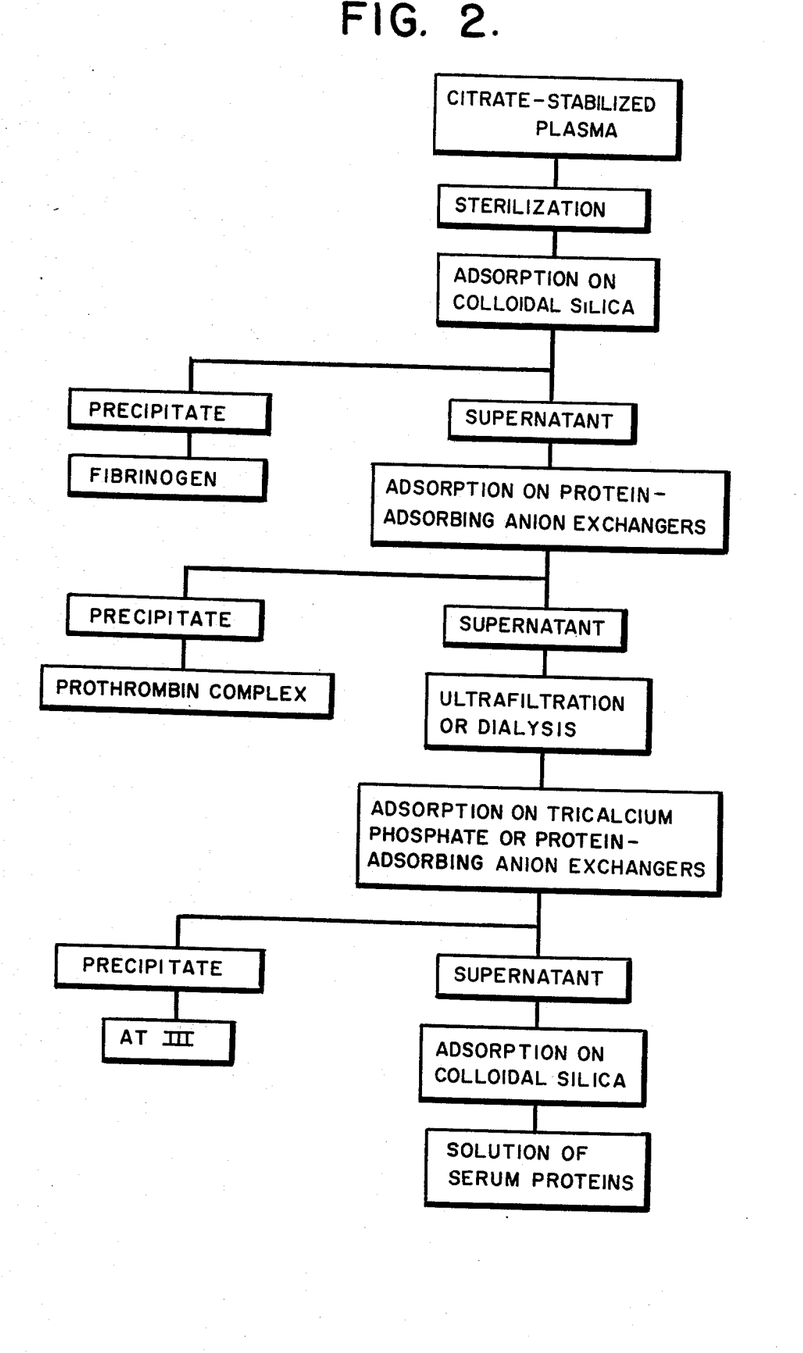
FIG. 2 is a flow sheet of a second process.

Referring now more particularly to FIG. 2, the method according to the invention for making the coagulation factors II, VII, IX and X, fibrinogen and antithrombin III can also be realized when from the citrate plasma (possibly after removal of cryoprecipitate) there are first removed the coagulation factors II, VI, IX and X (PPSB) by adsorption with protein-adsorbing anion exchangers and the said plasma is then mixed with colloidal silica for adsorption of fibrinogen. In this procedure, however, the frequently simultaneously occurring fibrinolysis may adversely affect the fibrinogen extraction. The "citrate plasma" separated from the colloidal silica then serves, after its ultrafiltration, as starting material for obtaining antithrombin III and the solution of serum proteins, antithrombin III being obtained by adsorption on tricalcium phosphate or protein-adsorbing anion exchangers and subsequent elution.

Figure 2A:
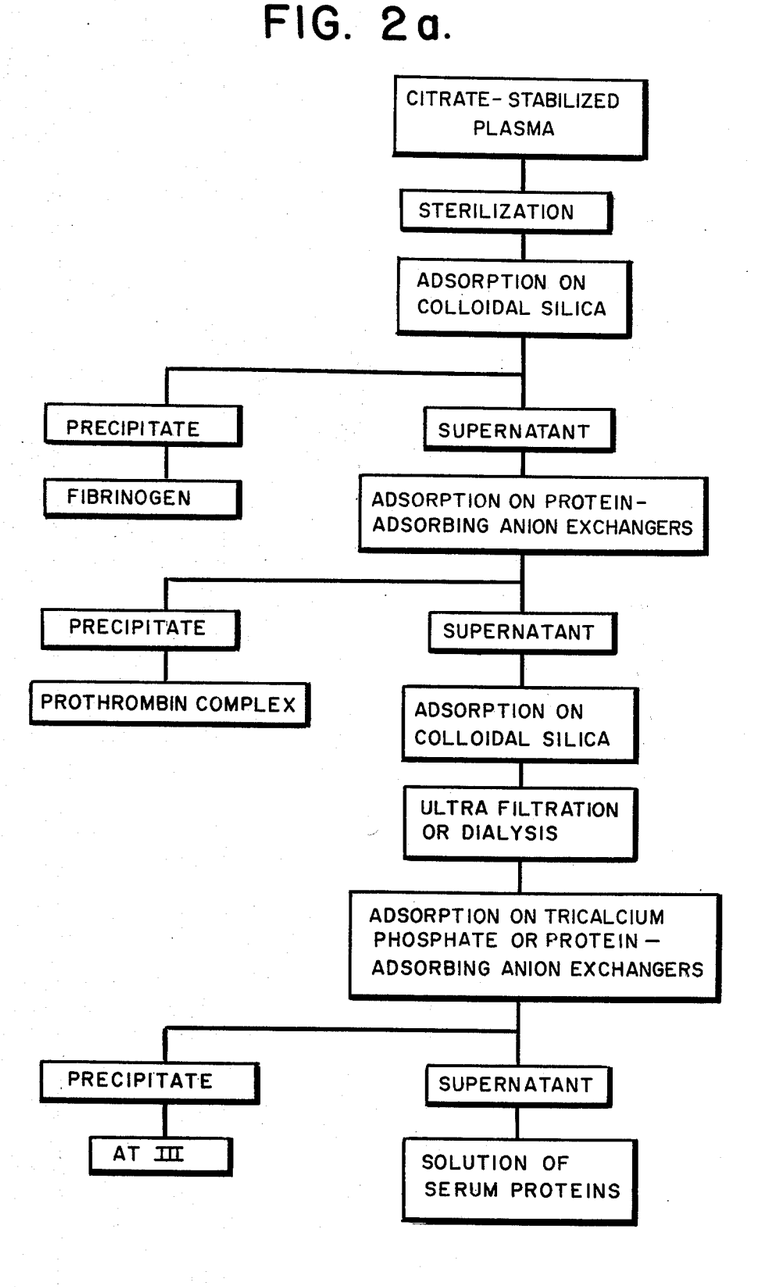
FIGS. 2a and 2b are flow sheets of variants of FIG. 2.
Figure 2B:
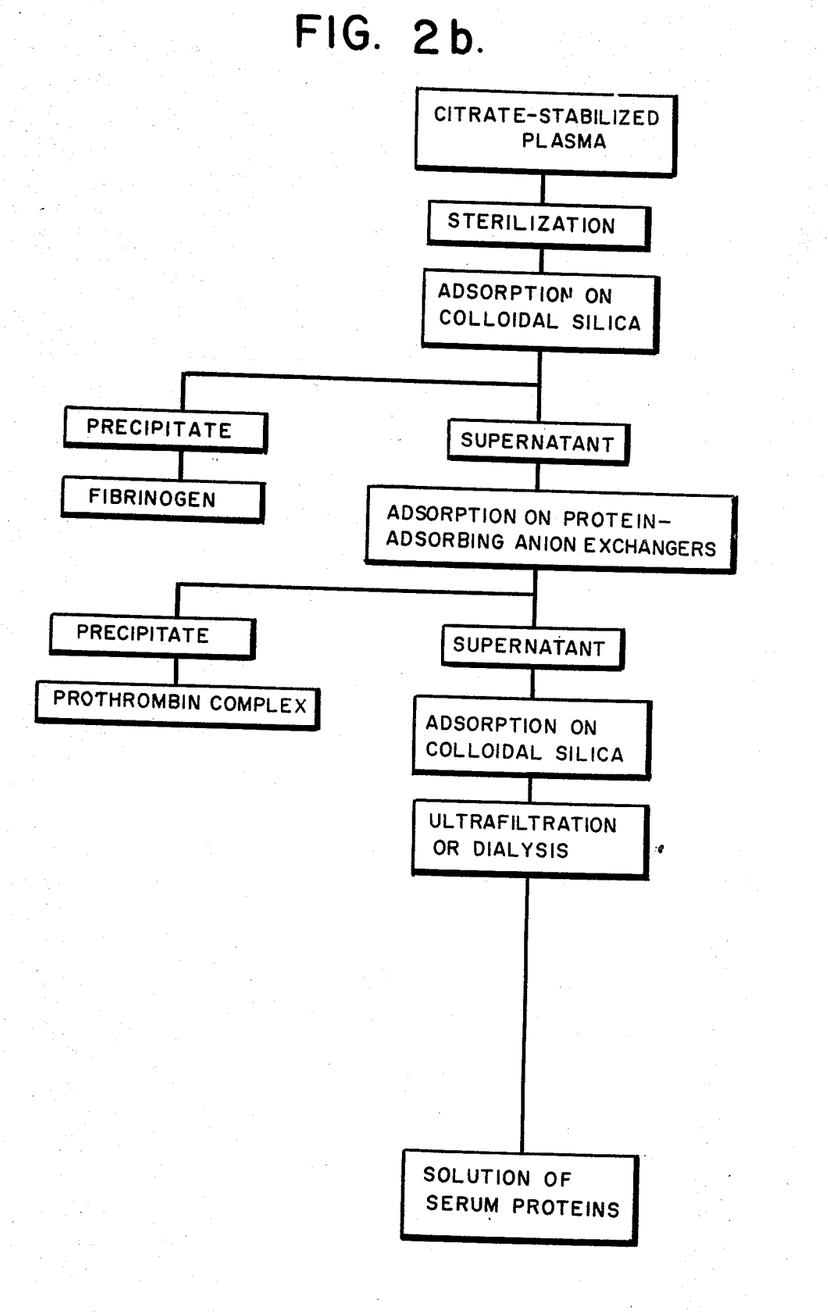
Figure 3:
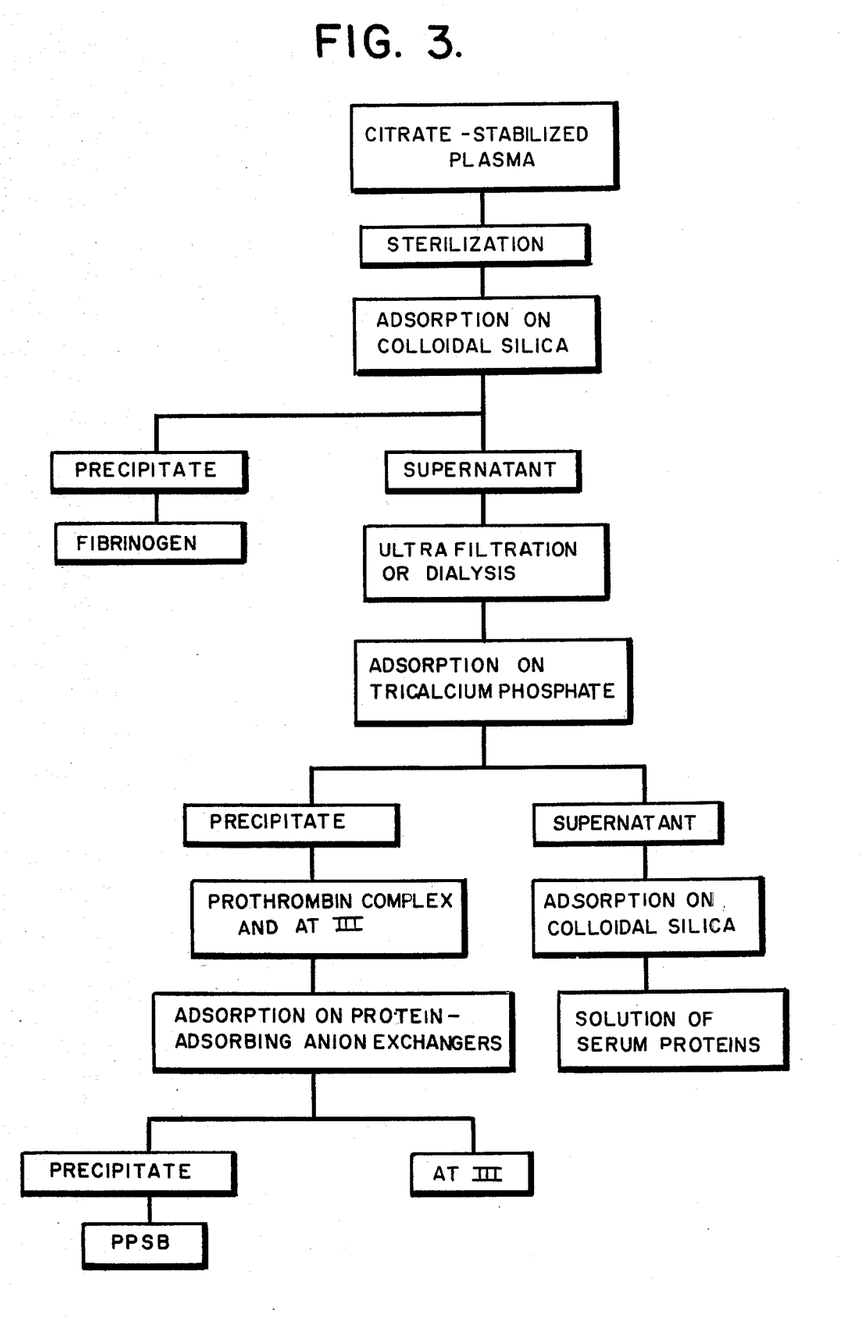
FIG. 3 is a flow sheet of a variant of FIG. 1.
Figure 4:
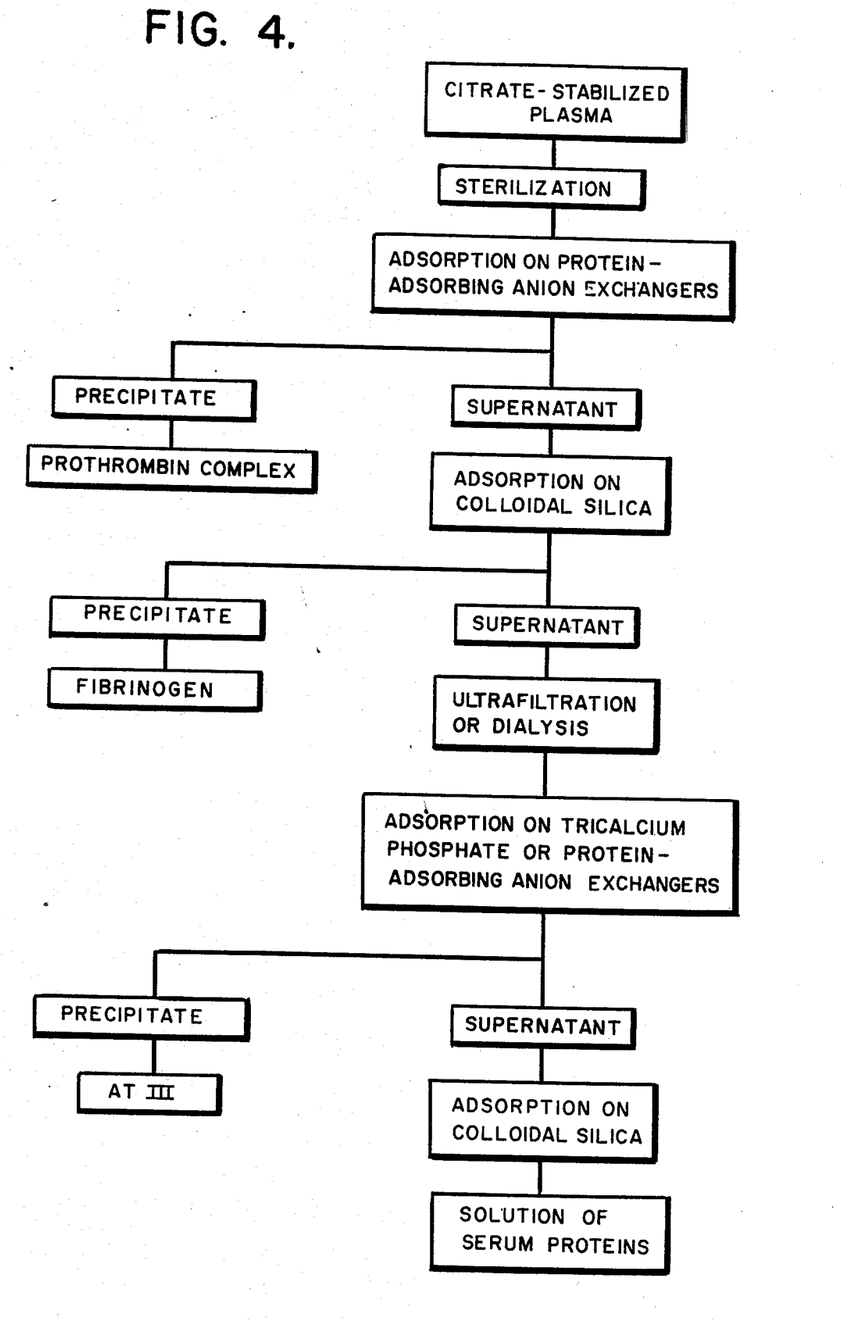
FIG. 4 is a flow sheet of a third process.

FIGS. 2a and 2b show variants of FIG. 2 wherein the antithrombin III is not separated from the solution which at some stage is given a second treatment with colloidal silica. FIGS. 3 and 4 show further embodiments of the invention, the sequence of adsorption and ultrafiltration steps having been changed. Common to all embodiments of the method according to the invention is that a citrate plasma, by adsorption with colloidal silica and subsequent ultrafiltration or dialysis, is brought into the most favorable form which, in avoiding the fractionating methods as customary in protein fractionation all of which adversely affect the native structure of the proteins, makes possible the simultaneous production of several coagulation-active products and a coagulation-inert solution of serum proteins.

According to the invention, a plasma stabilized with citrate is used as starting material. From this plasma, there can at first be obtained, by thawing at temperatures near +4° C. in known per se manner, a cryoprecipitate which can then be processed further into concentrates of antihemophilic globulin A. After being freed from the cryoprecipitate, the plasma can then be used for the method according to the invention. It is possible, however, to use a citrate plasma which has not been previously freed from cryoprecipitate. The citrate plasma used thus need not first be deep-frozen and, if it was deep-frozen, can be quickly thawed to temperatures of +37° C. and used directly in the method according to the invention.

Preferably, a citrate plasma is used which was frozen after its extraction and which is thawed at temperatures between 0° and 8° C. or +37° C. The particular thawing temperature chosen will determine whether in a particular case more importance is attached to making cryoprecipitate and/or antihemophilic globulin A or to making fibrinogen. Although both products can be produced in the same overall process, the fibrinogen yield from plasma freed from cryoprecipitate is clearly less than from plasma from which the cryoprecipitate had not been removed, since cryoprecipitate, as is known, contains a great amount of fibrinogen. Prior to adsorption of the plasma with colloidal silica, it is treated in known manner at pH values of between 6.5 and 8.0 with beta-propiolactone and then with ultraviolet radiation so as to assure safety of the products from hepatitis. The colloidal silica-adsorbed "citrate plasma" from which the PPSB factors had possibly already been removed by adsorption on anion exchangers that adsorb proteins, can be processed further according to one of the embodiments of the drawings.

As opposed to the known methods, the method according to the invention has the following advantages:

1. The citrate plasma used as starting material is usually obtained during blood donations and plasmaphoresis and thus constitutes a relatively readily available source of supply.

2. There are avoided the problems and costs of sterilizing and keeping polystyrene-based ion exchangers pyrogen-free on a commercial scale as is required for production of ion exchanger plasma.

3. There are avoided the problems of polystyrene-based ion exchanger resins, e.g. abrasion and possible liberation of low-molecular components from the resins.

4. The fibrinogen as obtainable by the method according to the invention is not yet degraded through fibrinolysis, as is usually the case with plasma solutions from which the fibrinogen has not been removed immediately after thawing of the plasma.

The invention will now be more fully explained in the examples that follow:

EXAMPLE 1

A. Preparation of antihemophilic globulin A-containing concentrate

9 Parts by volume of donor venous blood were added to 1 part of a 3.8%-sodium citrate stabilizer solution. The blood was centrifuged as quickly as possible after its withdrawal and the erythrocytes suspended in physiological common salt solution reinjected into the donor. The plasma was frozen within 48 hours at −40° C.

The frozen plasma was thawed at a temperature of +2° to +4° C. The centrifuging was effected through single vessel centrifuging. From the so obtained cold precipitation (cryoprecipitate) a concentrate was produced in known manner which contained the antihemophilic globulin A.

B. Preparation of hepatitis-safe fibrinogen

The cryoprecipitate-free citrate plasma pool obtained in step A at the centrifuging was mixed at room temperature with freshly distilled beta-propiolactone to a concentration of 0.25 vol.-%. The mixture was stirred for one hour at room temperature and during this time the pH value maintained at 7.2 through continuous addition of 1 N NaOH solution. After ultraviolet radiation with a UV flowthrough radiation unit (dill apparatus) the hydrolysis of the beta-propiolactone was completed through continuous addition of 1 N NaOH while maintaining the pH value constant, until a constant pH was achieved without any further NaOH addition. The beta-propiolactone-treated and UV-irradiated citrate plasma was cooled to 4° C. and mixed with "Aerosil 380" to a concentration of 1.5 g colloidal silica/100 ml plasma or 250 mg per g protein. The mixture was then centrifuged and the precipitate processed further to obtain fibrinogen, while the supernatant was used as atarting material for the preparation of PPSB/AT III and a solution of stable serum proteins.

The Aerosil precipitate was washed with physiological common salt solution and then the fibrinogen eluted with a citrate-containing 15%-NaCl solution at pH 9.5. This fibrinogen solution was then ultrafiltered for the removal of the high common salt concentration. The ultrafiltered fibrinogen solution was further purified by an ethanol precipitation analogous to the Cohn fractionation. The ethanol-precipitated fibrinogen was dissolved in citrate-containing physiological common salt solution, then sterilized by filtration and freeze-dried.

C. Preparation of AT III-containing prothrombin complex 10 l fibrinogen-free citrate plasma as obtained in accordance with the procedure of step B were ultrafiltered at room temperature, a dialysis against 0.45%-NaCl solution being effected (by way of the hollow fiber system of the Amicon company) and the plasma volume being first concentrated down to ⅔ the original volume. The 10 l plasma were thus within a period of 15 minutes concentrated down to 7 l and then dialyzed within a period of 3 hours against 70 l 0.45%-NaCl solution. Under these conditions, the citrate concentration sank from 60 meq/l to below 1 meq/l. By addition of 0.45%-NaCl solution, the original volume was then restored. This fibrinogen-freed and ultrafiltered "citrate plasma" served as starting material for the preparation of the AT III-containing PPSB concentrate.

By addition of tricalcium phosphate up to a concentration of 0.8 wt.% to the above protein solution and stirring of this mixture at +4° C. for 45 minutes and subsequent centrifuging in beakers, the AT III-containing PPSB was separated by elution with a 0.05 M trisodium citrate solution from the tricalcium phosphate precipitate, while the supernatant of the tricalcium phosphate precipitate served as starting material for the preparation of the solution of stable serum proteins.

The AT III-containing PPSB solution was either directly processed further into an AT III-containing PPSB concentrate or served as starting material for making PPSB and an AT III preparation.

If an AT III-containing PPSB concentrate was produced, then the tricalcium phosphate eluates were adsorbed with colloidal silica (0.5 wt.%) and the PPSB/AT III-containing solution, after removal of the colloidal silica by centrifuging, concentrated down with an ultrafiltration apparatus until the factor IX-activity of the solution amounted to 30 units per ml.

D. Preparation of AT III and PPSB concentrate

The AT III-containing PPSB solution as obtained in step C was dialyzed against 0.9%-NaCl solution, the citrate concentration sinking thereat to a value of 40 meq/l. Out of this solution, by adsorption with DEAE-Sephadex ®A 50 (Diethylaminoethyl-Sephadex, trademark of Pharmacia Fine Chemicals for a dextran cross-linked with epichlorohydrin), the PPSB factors were adsorbed and then eluted at pH 7.0 with a 2 M NaCl solution which contained 0.01 M citrate. The DEAE-Sephadex A 50 supernatant contained the AT III and by concentration through ultrafiltration was brought to a concentration ten times that of a normal plasma, sterilized by filtration and freeze-dried.

E. Preparation of a solution of stable serum proteins

The residual plasma left over in step C as supernatant of the tricalcium phosphate precipitate was mixed for 3 hours at 45° C. with colloidal silica (Aerosil 380 of Degussa) in a proportion of 2 g Aerosil 380 per 1 l plasma, and stirred. The colloidal silica was then separated in beakers by centrifuging. The protein solution was ultrafiltered and concentrated to a protein concentration of 5 g/100 ml.

This protein solution was then, over hot air-sterilized membrane filters of 0.45 pore size and 0.22μ, filled into empty sterile bottles.

EXAMPLE 2

The procedure of Example 1 was repeated with the exception that the cryoprecipitate was not removed from the starting plasma.

EXAMPLE 3

The procedure of Example 1 was repeated for steps A, B, C and E, while in step D, in the preparation of AT III and PPSB from the AT III-containing PPSB solution, the latter was first concentrated by ultrafiltration down to 1/5 its original volume before adsorption of the PPSB with DEAE-Sephadex A 50 was effected.

EXAMPLE 4 (According to FIG. I)

The procedure of Example 1 was repeated for steps A and B.

C. Preparation of AT III and AT III-containing prothrombin complex 10 l fibrinogen-free citrate plasma as obtained by the procedure of step B of Example 1 were ultrafiltered according to the procedure of step C of Example 1.

The so obtained ultrafiltered plasma was adsorbed at a pH value of 7.2 under stirring with 0.5 g DEAE-Sephadex A 50 per l plasma that had previously been treated as follows:

150 g DEAE-Sephadex A 50 were swelled for about 20 hours in 10 l of distilled water. The water standing over the swelled gel was sucked off and replaced with fresh water. The gel was stirred and, after settling, the fine, still suspended particles sucked off. This procedure was repeated once. Following that, the swelled and water-suspended gel was sterilized for 20 minutes at 121° C.

After adsorption on the DEAE-Sephadex A 50, the plasma was sucked off of the Sephadex and served as starting material for the further processing to AT III and the solution of serum proteins.

The Sephadex A 50 was washed twice with a physiological common salt solution and then eluted per 0.5 g of Sephadex A 50 (dry weight) for 20 minutes at room temperature with 100 ml of a 0.01 M citrate buffer of a pH value 7.0 which was 0.2 M on NaCl, which had been obtained as follows:

11.69 g NaCl and 2.29 g trisodium citrate were dissolved in about 800 ml $H_2O$. The pH value was adjusted to 7.0 by addition of 1 N HCl. This solution was brought to 1 l with $H_2O$.

This elution was repeated. The combined AT III-eluates were initially concentrated with an ultrafiltration apparatus (by Amicon) using an ultrafiltration cartridge.

Following that, the PPSB factors were eluted from the DEAE-Sephadex A 50. This elution was effected by stirring with 10 ml of a 0.01 M citrate buffer of a pH of 7.0, which was 2 M on NaCl, per 0.5 g Sephadex A 50 (dry weight) for 20 minutes at room temperature. The buffer solution used for that purpose was obtained as follows:

116.9 g NaCl and 2.29 g trisodium citrate were dissolved in about 800 ml $H_2O$. The pH value was adjusted to 7.0 by addition of 1 N HCl. This solution was brought to 1 l with $H_2O$.

The elution was repeated. The initial concentration of the eluates was effected with an ultrafiltration apparatus (by Amicon) using an ultrafiltration cartridge (Amicon SM 10). The retention from the initial concentration was checked with the coagulation activity measurement for activities of the PPSB factors. After that, the PPSB concentrate was mixed with 5 units heparin/ml and sterilized by filtration.

When dissolving the so obtained PPSB concentrates after drying in distilled water the properties as given in the following Table VI were obtained.

TABLE VI

| Properties of the PPSB concentrate | | | | | | | | |
|---|---|---|---|---|---|---|---|---|
| Protein g % | $Na^+$ meq/l | $Cl^-$ meq/l | Citrate meq/l | $Ca^{++}$ meq/l | Activity in % of the norm | | | |
| | | | | | II | VII | IX | X |
| about 2.5 | 140 | 125 | 110 | 45 | 2300 | 1800 | 2500 | 2500 |

A fact to be considered in evaluating the data of Table VI is that the volume of the dissolved PPSB preparation is about 10% greater than the originally used volume (volume increase through solid matter).

The PPSB concentrate had an AT III content that was about 2 to 4 times as high as that of a normal plasma. The $TGt_{50}$ of such a preparation was several hours.

D. Preparation of AT III (a) by adsorption on tricalcium phosphate

The plasma sucked off in step C from the Sephadex after adsorption on the DEAE-Sephadex A 50 was brought with 1 N NaOH to a pH of 8.0 and mixed with 0.8 wt.% tricalcium phosphate ($Ca_5 (PO_4)_3OH$, pentacalcium hydroxytriphosphate, molecular weight 502.32, art.no.2143 by Merck). Prior to use, the tricalcium phosphate was heated for 2 hours at 180° C. The adsorption time was 40 minutes. The subsequent separation of the tricalcium phosphate from the plasma was effected by centrifuging with a flowthrough centrifuge.

The plasma supernatant was used as starting material for step E.

To elute the antithrombin III from the tricalcium-phosphate precipitate, the latter was first washed for a period of 10 minutes by stirring with about 33 vol.% of 0.9%-NaCl solution, relative to the initial volume of plasma. Following that, centrifuging took place. Following that, the AT III was eluted by stirring for 30 minutes at room temperature with 5 vol.%, relative to the ultrafiltered plasma, of 0.05 M trisodium citrate-2-hydrate (Merck) at a pH of 8.8 to 9.1. The tricalcium phosphate was then separated by centrifugation from the AT III-solution. A second elution of the tricalcium phosphate precipitate analogously to the first elution was then carried out. The volume of eluent used was 2.5 vol.%, relative to the ultrafiltered plasma.

Following that, an initial concentration of the AT III-solution by ultrafiltration with an ultrafiltration apparatus (by Amicon), using an ultrafiltration cartridge (Amicon PM 10), was carried out at room temperature. The retention from the initial concentration of the solution showed an approximately 10-fold AT III enrichment vis-a-vis normal plasma.

Dissolving of the thus obtained, dried AT III-concentrate in distilled water gave the following analyses:

TABLE VII

| | Properties of the AT III concentrate | | | | |
|---|---|---|---|---|---|
| Protein g % | Na+ meq/l | Cl− meq/l | Citrate meq/l | Ca++ meq/l | AT III in IU/ml |
| about 4.0–5.0 | 140 | 25 | 110 | 45 | 200 |

A fact to be considered in evaluating the data of Table VII is that the volume of the dissolved AT III preparation is about 10% greater than the originally used volume (volume increase through solid matter).

(b) by adsorption on DEAE-Sephadex A 50 or DEAE-Cellulose

The procedure described in step D (a) was repeated with the exception that instead of tricalcium phosphate DEAE-Sephadex A 50 or DEAE-Cellulose was used as adsorbent.

An analogous antithrombin III-concentrate was obtained.

E. Preparation of a solution of stable serum proteins

The plasma remaining in step Da) as supernatant of the tricalcium phosphate precipitate was adsorbed during 3 hours at +45° C. with 2% Aerosil AE 380 and then centrifuged for a separation of the Aerosil. For a purification of this protein solution, the latter was passed over hot air-sterilized membranes of 5.0μ pore size.

To reduce the silicate, calcium and phosphate content of the purified solution, it was unfiltered at about +20° C. using ultrafiltration cartridges (Amicon PM 10). The ultrafiltered protein solution was then poured through hot air-sterilized membrane filters of 0.45 and 0.22μ pore size into empty, sterile 1 l bottles.

The plasma remaining in step D (b) as supernatant of the precipitate from DEAE-Sephadex A 50 was adsorbed on Aerosil AE 380 in the same manner as described before, ultrafiltered and sterile-filtered (sterilized by filtration) to obtain a solution of stable serum proteins.

It will be appreciated that the instant specification and claims are set forth by way of illustration and not limitation, and that various modifications and changes may be made without departing from the spirit and scope of the present invention.

What we claim is:

1. A method for obtaining fibrinogen, a prothrombin complex containing coagulation factors II, VII, IX and X, antithrombin III, and a solution of stable serum proteins from a citrate-stabilized blood plasma comprising contacting the plasma with colloidal silica of a specific surface of about 50 to 400 m²/g, about 50 to 400 mg of silica being employed per g of plasma protein, thereby to adsorb the fibrinogen from the plasma, separating the silica and adsorbed fibrinogen from the residual protein solution, subjecting the residual protein solution to ultrafiltration or dialysis so as to remove citrate and calcium ions therefrom, contacting the residual protein solution with an adsorbent for the prothrombin complex and antithrombin III, and separating the adsorbent with material adsorbed thereon from the residual solution of stable serum proteins.

2. A process according to claim 1, wherein the adsorbent for the prothrombin complex and antithrombin III is an anion exchanger formed of cross-linked cellulose or dextran carrying diethylaminoethyl groups.

3. A process according to claim 1, wherein the adsorbent for the prothrombin complex and antithrombin III is tricalcium phosphate.

4. A process according to claim 1, including the further steps of selectively eluting antithrombin III from the adsorbent with a citrate/NaCl buffer of low molarity, and then eluting the coagulation factors II, VII, IX and X with a citrate/NaCl buffer of higher molarity.

5. A process according to claim 1, including the further step of subjecting the residual solution of stable serum proteins to a second adsorption thereby to adsorb additional antithrombin III, and then eluting the additional antithrombin III from the second adsorbent.

6. A process according to claim 1, including the further step of contacting the colloidal silica carrying adsorbed fibrinogen with an alkali halide solution thereby to elute the fibrinogen.

7. A process according to claim 1, wherein the blood plasma prior to contact with the colloidal silica is treated with beta-propiolactone and UV radiation.

8. A process according to claim 7, wherein about 150 to 250 mg of colloidal silica are employed per g of plasma protein, the process including the further steps of contacting the colloidal silica carrying adsorbed fibrinogen with an alkali halide solution thereby to elute the firinogen, selectively eluting the coagulation factors II, VII, IX and X with a citrate/NaCl buffer of higher molarity, subjecting the residual solution of stable serum proteins to a second adsorption thereby to adsorb additional antithrombin III, and then eluting the additional antithrombin III from the second adsorbent.

9. A method for obtaining fibrinogen, a prothrombin complex containing coagulation factors II, VII, IX and X, antithrombin III, and a solution of stable serum proteins from a citrate-stabilized blood plasma comprising contacting the plasma with a first selective adsorbent for coagulation factors II, VII, IX and X but not for antithrombin III, separating the first adsorbent from the liquid, contacting the liquid with colloidal silica of a specific surface of about 50 to 400 m²/g, about 50 to 400 mg of silica being employed per g of protein thereby to adsorb the fibrinogen, subjecting the liquid to ultra-filtration or dialysis so as to remove citrate and calcium ions therefrom, and contacting the liquid with a second selective adsorbent to adsorb the antithrombin III and leave a solution of stable serum proteins.

10. A process according to claim 9, wherein the selective adsorbent for coagulation factors II, VII, IX and X is an anion exchanger formed of cross-linked cellulose or dextran carrying diethylaminoethyl groups.

11. A process according to claim 9, wherein the blood plasma prior to contact with the first selective adsorbent is treated with beta-propiolactone and UV radiation.

12. A process according to claim 9, including the further step of contacting the colloidal silica carrying adsorbed fibrinogen with an alkali halide solution thereby to elute the fibrinogen.

13. A process according to claim 10, wherein the blood plasma prior to contact with the first selective adsorbent is treated with beta-propiolactone and UV radiation, about 150 to 250 mg of colloidal silica are employed per g of plasma protein, the process including the further steps of contacting the colloidal silica carrying adsorbed fibrinogen with an alkali halide solution thereby to elute the fibrinogen, and eluting the antithrombin III and the coagulation factors from their respective adsorbents with a citrate/NaCl buffer solution.

14. A method for obtaining fibrinogen, a prothrombin complex containing coagulation factors II, VII, IX and X, antithrombin III, and a solution of stable serum proteins from a citrate-stabilized blood plasma comprising contacting the plasma with colloidal silica of a specific surface of about 50 to 400 $m^2/g$, about 50 to 400 mg of silica being employed per g of plasma protein, thereby to adsorb the fibrinogen from the plasma, separating the silica and adsorbed fibrinogen from the residual protein solution, contacting the residual protein solution with an anion exchanger thereby to remove citrate from the solution, separating the anion exchanger and adsorbed prothrombin complex from the residual solution, and subjecting the residual solution to ultrafiltration or dialysis to remove calcium ions therefrom.

15. A process according to claim 14, including the subsequent step of contacting the residual solution with an adsorbent for the antithrombin III, and separating the adsorbent with material adsorbed thereon from the residual solution of stable serum proteins.

16. A process according to claim 14, wherein after separation of the anion exchanger and before ultrafiltration of dialysis the solution is contacted with additional colloidal silica which is then separated with whatever is adsorbed thereon.

* * * * *

UNITED STATES PATENT AND TRADEMARK OFFICE
CERTIFICATE OF CORRECTION

PATENT NO. : 4,272,523
DATED : Jun. 9, 1981
INVENTOR(S) : Ronald Kotitschke et al It is certified that error appears in the above-identified patent and that said Letters Patent are hereby corrected as shown below:

Column 14, line 11 Delete "of" and insert --or--.

Signed and Sealed this

Twenty-second Day of December 1981

[SEAL]

Attest:

GERALD J. MOSSINGHOFF

Attesting Officer     Commissioner of Patents and Trademarks